United States Patent [19]

Riggs

[11] Patent Number: 4,948,897

[45] Date of Patent: Aug. 14, 1990

[54] METHOD OF PREPARATION OF 2,6-BIS(PICRYLAMINO)-3,5-DINITROPYRIDINE

[75] Inventor: Robert S. Riggs, Grand Prairie, Tex.

[73] Assignee: Jet Research Center, Inc., Arlington, Tex.

[21] Appl. No.: 335,158

[22] Filed: Apr. 7, 1989

Related U.S. Application Data

[62] Division of Ser. No. 131,971, Dec. 11, 1987, Pat. No. 4,855,436.

[51] Int. Cl.$^5$ ............................................. C07D 213/74
[52] U.S. Cl. ..................................... 546/307; 149/92; 149/105; 149/109.6
[58] Field of Search ...................... 149/92, 105, 109.6; 546/307

[56] References Cited

U.S. PATENT DOCUMENTS 3,678,061 7/1972 Coburn ................................. 546/307
4,564,405 1/1986 Pallanck ................................. 149/21

FOREIGN PATENT DOCUMENTS 0104717 4/1984 European Pat. Off. ............ 546/307

OTHER PUBLICATIONS

Adenis et al., "Syntheses and Properties of Some Thermally Stable Initiating Explosives", E.S.A., SP-144, 1980, pp. 69-76.

*Primary Examiner*—Mary C. Lee
*Assistant Examiner*—Zinna Northington-Davis
*Attorney, Agent, or Firm*—Robert A. Kent

[57] ABSTRACT

A method for preparing 2,6-bis(picrylamino)-3,5-dinitropyridine (PYX) which includes the steps of first dissolving crystalline PYX in a primary solvent in which the solvent used is selected from the group consisting of pyridine, dimethylformamide, methylsulfoxide or mixtures thereof. The primary solvent system is then combined with a second solvent in which the PYX is substantially insoluble, but which, in admixture with the primary solvent, forms a true solution of the PYX, referred to as the secondary solution. A third solvent is then added to the binary solvent system, which third solvent is soluble with the binary solvent system but which promotes precipitation of PYX in a form which exhibits improved characteristics as an explosive.

6 Claims, No Drawings

METHOD OF PREPARATION OF 2,6-BIS(PICRYLAMINO)-3,5-DINITROPYRIDINE

This is a divisional of Ser. No. 131,971, filed 12/11/87, now U.S. Pat. No. 4,855,436.

BACKGROUND OF THE INVENTION

1. Field of the Invention

This invention relates to a method for preparing 2,6-bis (picrylamino)-3,5-dinitropyridine (PYX) which is a reliable explosive material of improved effectiveness as compared to the PYX prepared by methods previously in use.

2. Brief Description of the Prior Art

It has characteristically been difficult to initiate the detonation of many high temperature explosives. This problem of detonation initiation difficulty may be quantified by the results of a test which is referred to in the art as "air gap" sensitivity. A well known, widely used high temperature, thermally stable explosive and propellant is 2,6-bis(picrylamino)-3,5-dinitropyridine (hereinafter referred to as PYX). PYX exhibits relatively poor detonation initiation under some conditions of use.

This commercially available material is used to manufacture high temperature oil and gas well perforators and detonating cord. The perforators and detonating cord are typically fixed inside tubular perforating guns lowered into the well. Several guns may be connected together axially. Where such is the case, the gun-to-gun interconnection schemes utilized at present require that a detonating cord extend from one gun to another, and be able to propagate its detonation across air gaps in the tandem assembly of guns, thereby making its firing connection to the next gun in the series. Failure of detonation transfer frequently occurs at these air gaps, but such failures can be reduced to some degree by placing boosters of purified PYX at the air gap interfaces. Another frequent site of failure of detonation continuity occurs where the detonation must be propagated from the detonating cord to the perforator, and even here the slightest misalignment between the cord and the perforator may result in failure. It has been experienced that the purified PYX which is commercially available is not adequately sensitive to prevent and eliminate misfires occurring at the described sites. There is, accordingly, a need to improve the PYX so as to increase its shock sensitivity, and to reduce the frequency of detonation failure when this otherwise excellent explosive material is utilized.

It is also known that both the shape and size distribution of crystalline explosive particles are often important characteristics in determining the safety with which the explosive can be used, its sensitiveness, and the uses to which it can be most effectively put. Because of such considerations, explosives are produced by various procedures in an endeavor to achieve the explosive product in an optimum physical form in terms of the sought characteristics and the intended use. Variations in the formulation technique result in variations in the granulation and crystal morphology of the explosive product crystals, and result in improvement in the powder flow, bulk and pressed density, and in the dusting properties of the explosive.

In the case of PYX, the basic process by which this explosive was originally produced commercially is described in Coburn U.S. Pat. No. 3,678,061. Certain disadvantages and difficulties attended the Coburn method of PYX production, however, including the production of undesirable corrosive by-product acids as the two-step reaction proceeded, and the production of a final PYX product which demonstrated less than optimum thermal stability.

A subsequent effort to improve the properties of the PYX product is described in European Patent Application 0 104 717 of Hudson, published Apr. 4, 1984. The Hudson European Patent Application, as published, described a procedure involving two reaction steps, in the first of which 2,6-diaminopyridine is reacted in a polar protic solvent with a picrylating compound in the presence of an alkaline earth metal carbonate to yield as an intermediate compound, 2,6-bis(picrylamino)pyridine. By this procedure of producing the intermediate compound, the production of undesirable by-product acids is substantially reduced as compared to the yield of such acids in the practice of the Coburn process, and the presence of an alkali or alkaline earth carbonate or bicarbonate effectively removes the small amount of such undesirable product as is produced The intermediate compound, 2,6-bis(picrylamino)-pyridine is readily isolated in good yields, and extensive purification is not required prior to performing the second reactive step which entails the nitration of the intermediate compound with concentrated nitric acid. The rapid separation of the intermediate which can be realized enables the nitration step to be carried out without the need for recrystallization of the intermediate prior thereto.

Following nitration of the intermediate with concentrated nitric acid, a yield of the order of ninety percent is realized, and the PYX crystals produced have a higher thermal stability than those which are produced according to the method of Coburn U.S. Pat. No. 3,678,061.

This procedure for producing PYX in which the initial reaction is carried out in a polar, protic solvent in the presence of an alkali metal bicarbonate is also described in J. C. Adenis et al "*Synthesis and Properties of Some Thermally Stable Initiating Explosives*" European Space Agency, ESA SP-144, 1980, pages 69–76.

A yet more recent technique used for modifying the form of crystalline PYX explosive is that of recrystallization or reformation from certain specific types of solvent systems. In Pallanck U.S. Pat. No. 4,564,405, a method is disclosed for producing improved, thermally stable PYX by treating certain crystalline forms of PYX with dimethylsulfoxide (DMSO) to form an intermediate adduct compound. The adduct compound is then dissociated into either cubic crystalline particles or an agglomerate of spherical particles of PYX material. The addition compound of DMSO is formed by adding one molar proportion of PYX to about thirty moles of solvent DMSO at a temperature of from about 100° C. to about 110° C.

The resultant solution is cooled to obtain a slurry of the adduct crystals, and these are then recovered by filtration, and are then dissociated by one of several methods. The method of dissociation used will determine what type of PYX product is formed. In one type of dissociation, a solvent which is miscible with DMSO, but in which the PYX has only very slight solubility, is added to the DMSO to cause the precipitation of an agglomerate form of PYX. Alternatively, cubic crystalline particles of PYX are obtained by subjecting the recovered adduct crystals to heat or vacuum, or a combination of heat and vacuum.

The PYX material derived from the DMSO adduct is a superior explosive as compared to other commercially available needle-shaped crystals of PYX because it has improved thermal stability, and is of increased density. The uniformity of the particles also makes the product easy to pour and to handle, and it has a reduced tendency to acquire a static charge. The process described in Pallanck U.S. Pat. No. 4,564,405 has enhanced the sensitivity of the PYX produced thereby, and thus has enabled detonation failures at air gap interfaces to be reduced. Such failures are not completely eliminated, however, when PYX produced by the Pallanck process is used, and moreover that material is not available is large quantities.

SUMMARY OF THE INVENTION

The present invention provides a new process for producing PYX explosive of increased shock sensitivity. The process generally entails the recrystallization of the PYX crystals from a tertiary solvent system after a certain sequence of steps involving the use of certain primary and secondary solvents. The PYX produced by the described method of the invention is capable of propagating detonations across air gaps that are approximately several times greater than those across which detonation may be effectively propagated by the types of PYX material previously available.

Broadly described, the process of the present invention entails initially dissolving commercially available PYX in an organic primary solvent. The PYX crystals, at this stage of the process, can be dissolved in pyridine, dimethylformamide, methylsulfoxide, or mixtures of these solvents. After this initial solution of the explosive crystals in one or more of the described organic primary solvents, the PYX solution is then combined with a secondary solvent. This secondary solvent is one in which the PYX is not normally considered to be soluble beyond trace amounts. In addition to this characteristic inability to significantly dissolve the PYX crystals, the second solvent is further characterized by its ability to form, by the described addition, a transparent binary solvent system in which the PYX crystals are soluble. Secondary solvents which can be used with various of the primary organic solvents described include various ketones, esters, alcohols, mercaptans or certain heterocyclic compounds, as well as mixtures thereof.

As a final step of the method of the invention, PYX crystals in the highly sensitized form are precipitated first colloidally and then suspensionally from the transparent binary solvent system by adding a third solvent to such binary solvent system. The third solvent is miscible with the binary solvent system and forms with it a ternary solvent system. The ternary solvent system formed, however, is ineffective to retain the PYX in solution, and the result is that crystals of the highly sensitized PYX material are precipitated from the ternary solvent system. The most commonly used ternary solvent employed is water.

The method of the present invention has been shown capable of repeatedly yielding in excess of 99 percent of the precipitated product which is sought, based on the weight of the starting PYX material, whereas the prior art processes, such as that disclosed and described in the Pallanck patent, generally achieve a yield no better than about 91 percent.

The invention also provides a method for producing PYX crystals of high explosive in good yield, and in a much shorter period of time than that which is required by the most effective prior methods of production of this material.

Additional objects and advantages of the invention will be discerned as the following detailed description of preferred embodiments of the invention is read.

DETAILED DESCRIPTION OF PREFERRED EMBODIMENTS OF THE INVENTION

In the first step of the method of the invention, from about 5 to about 50 parts of PYX, such as that produced by the method described in U.S. Pat. No. 3,678,061 to Coburn, is dissolved in about 100 parts of a primary solvent. Thus, the weight ratio of primary solvent to PYX ranges from about 2 to 1 to about 20 to 1, depending upon the solvent which is selected and the temperature which is utilized to effect dissolution. Primary solvents which can be very effectively utilized include pyridine, dimethylformamide, methylsulfoxide or mixtures of these organic solvents. The solvent which is preferably employed is methylsulfoxide (or DMSO).

The temperature used is preferably between about 70° C. and about 100° C., with from 80°–85° C. being the most preferred temperature range. After the mixture is brought up to the desired temperature, it is stirred until dissolution of the PYX in the solvent is complete.

After the PYX is completely dissolved in the primary solvent, the solution thus formed is admixed with a secondary solvent. A characteristic of the secondary solvent is that it will not dissolve any significant amount of the PYX if used independently as a primary solvent. Second, the combining of the PYX solution (in the primary solvent) with the secondary solvent must result in a true solution; that is, the secondary solvent must act as a diluent to the primary solvent system in forming a binary solvent solution.

A number of secondary solvents can be used, but each one is not universally usable with any one of the specified types of primary solvent. Thus, the particular secondary solvent selected will vary, depending upon the primary solvent which is used. Ethanol, for example, is an effective secondary solvent when the primary solution added into it is a solution of PYX in either pyridine or methyylsulfoxide, but ethanol is not usable if dimethylformamide is the primary solvent and the primary solvent PYX solution is added into the ethanol. Similar selectivity is characteristic of other secondary solvents which are limited in their usefulness to employment with certain ones of the primary solvents. Among the various secondary solvents which can be employed are various monohydroxy alcohols including, for example, methanol, ethanol and 2-propanol; monofunctional aldehydes such as acetaldehyde and benzaldehyde; certain esters, such as, for example, ethyl acetate, propyl acetate and butyl acetate; heterocyclic compounds, such as, for example, tetrahydrofuran and thiophene; ketones, such as, for example, 2-propanone (acetone), 2-butanone, cyclohexanone, and methylethyl ketone; and nitriles, such as, for example, acetonitrile. Mixtures of these secondary solvents can also be used. Especially useful solvents in this group are 2-propanone, methanol, tetrahydrofuran and ethyl acetate.

The amount of the secondary solvent employed should be at least equimolar to that of the solvated PYX. Typically, however, the secondary solvent to primary solvent volumetric ratio ranges from about 10:1 to about 20:1, and may effectively be even higher than this in some systems. The temperature at which the addition is made is from about 20° C. to about 100° C.

The addition is preferably made at ambient temperature, and generally only slight stirring is required in order to effect complete dispersion. The addition of the initial or primary solution to the secondary solvent results in the formation of a binary solvent-PYX solution.

In the case of some binary solvent systems, the effectiveness of the secondary solvent in meeting the previously described criteria may depend upon whether the primary solution of PYX is added to the secondary solvent, or, instead, the secondary solvent is added to the primary PYX solution. Thus, in the case of ethanol, a premature precipitate of the PYX will occur if a solution of PYX in dimethylformamide is added to the ethanol. If the ethanol is added to the solution of PYX in dimethylformamide, however, an orange solution will result, and the process can be continued through the step entailing the addition of a third solvent.

In the next step of the process of the invention, a third solvent is added to the binary solvent-PYX solution for the purpose of effecting precipitation of the PYX as the product sought. It is essential, in carrying out this step, that the PYX be abstracted from the binary solvent-PYX solution by adding the third solvent to it, instead of adding the binary solvent solution to the third solvent. Generally, the addition is made at ambient temperature with slight or gentle agitation. Higher temperatures can be used, with commensurate decrease in economic attractiveness. The third precipitating solvent is usually water; however, some compounds which are normally used as secondary solvents may also be used as the precipitating third solvent, depending upon the nature of the particular system. For example, methanol or isopropanol may be employed as a secondary solvent, and then may also be subsequently used to promote precipitation of PYX. Other tertiary solvents which can be used include ethylene glycol, glycerin, acetic acid and formic acid.

The quantity of the third solvent which is employed is normally and preferably at least equal volumetrically to that of the primary solvent, although precipitation can be effected in some degree with some systems by use of as little as 10 percent of that volume. With respect to the upper limit of the amount of tertiary solvent utilized, it does not appear that any amount is excessive in the sense of impeding the sought precipitation of the PYX.

EXAMPLE 1

Into a suitably sized reaction vessel equipped with a heater and stirrer, 100 cc of dimethylformamide are placed as the primary solvent. Ten grams of PYX are added to the solvent while stirring is continued until dissolution is complete. The transparent primary solution is then combined with 100 cc of ethanol as a secondary solvent. Light agitation of the system is employed to insure homogeneity. Then, 1000 cc of isopropanol is added to the binary solution of the PYX to precipitate the PYX crystals from the binary system. The crystals are recovered by filtration, and are then washed three times with 100 cc of ethanol at each washing. The PYX material is then dried at reduced pressure for a period of 8 hours. Drying is then continued at reduced pressure and 120° C. for an additional 8 hours.

The air gap sensitivity of the PYX material produced by the described precipitation with the isopropanol tertiary solvent is 1.5 inch.

The mechanism by which the PYX crystals precipitated by the tertiary solvent are sensitized is not understood with certainty. It is believed that the PYX and the primary solvent initially form a solvate; that is, a combination of a solute with its solvent in definite proportions. The introduction of the secondary solvent may then produce a solvated complex, which is the configuration of a substance unit intermediate between a chemical compound and a mechanical dispersion. Last, the tertiary solvent apparently breaks the solvate complex, resulting in the reformation of particulate PYX in a morphological configuration that is dictated by the nature of the solvent system selected. If this postulated mechanism of precipitation is accurate, then the precipitation must result in a material whose microstructure differs from the material precipitated from a concentrated system, such as in Pallanck U.S. Pat. No. 4,564,405.

EXAMPLE 2

Into a suitably sized glass reaction vessel are placed 1 part by weight of PYX and 5 parts by weight of methylsulfoxide. This mixture is heated to a temperature of between 80°–85° C. with concurrent stirring until dissolution is complete. The hot solution is then added to 100 parts of acetone and the mixture is stirred slightly to achieve homogeneity. Then, 40 parts of water are added to the binary solvent system and the resulting precipitate is recovered by filtration. The precipitate is washed with 20 parts of additional acetone and is dried at reduced pressure.

A comparison of the tertiary solvent process of this invention with the DMSO adduct process described in the Pallanck patent is set forth in Table I.

TABLE I

| PRESENT INVENTION | PALLANCK PROCESS |
|---|---|
| 1. 50 g PYX in 250 cc DMSO | 1. 50 g PYX in 250 cc DMSO |
| 2. Add to 4 liters acetone | 2. Cool 45 minutes to crystallize |
| 3. Add 2 liters H$_2$O | 3. Filter |
| 4. Filter | 4. Wash with acetone (40 cc) |
| 5. Wash with 1 liter acetone | 5. Suspend crystals in acetone (300 cc) |
| 6. Dry in vacuum | 6. Reflux 30 minutes |
|  | 7. Filter |
|  | 8. Wash with 10 cc acetone |
|  | 9. Air dry 4 hours at ambient temperature |
|  | 10. Dry 16 hours at 70° C. |
|  | 11. Dry 7 hours at 100° C. |
| Time Required: 30 minutes (to drying stage) | Time Required: 5 hours (to drying stage) |
| Yield 99+ percent | Yield 88 percent |

Table I illustrates a significant advantage of the process of this invention over the process disclosed in the Pallanck patent. This is the much shorter time required to process the material and yield highly sensitized PYX crystals. If identical samples of PYX are dissolved in DMSO, the Pallanck process will require, on average, from 4 to 5 hours, not counting the final drying time. The process of this invention, however, requires no more than 30 minutes in order to take the material from the state of initial dissolution in the primary solvent to the point of final drying in the oven.

In Table II, the air gap 50 percent reliability of PYX product made by the processes described in Coburn U.S. Pat. No. 3,678,061 and Pallanck U.S. Pat. No. 4,564,405 is compared with that of PYX material made in five different preparations carried out in accordance with the principles of the present invention, and utilizing the tertiary solvent, three-step process of this invention. The starting material used in the Pallanck process was the PYX product made by the process described in Coburn U.S. Pat. No. 3,678,061, as were the starting PYX crystals used in each of the five different preparations carried out in accordance with the principles of the present invention, using various solvent systems within the scope of the invention.

TABLE II

Comparison of Air Gap Sensitivities

| Method - Material | Air Gap 50 Percent Reliability |
| --- | --- |
| Coburn U.S. Pat. No. 3,678,061 | 0.50 |
| Pallanck U.S. Pat. No. 4,564,405 | 1.75 |
| Present Invention (Primary/Secondary/Tertiary) | |
| (a) DMF[1]/MeOH[2]/Isopropanol | 1.25 |
| (b) DMSO/THF[3]/$H_2O$ | 1.75 |
| (c) DMF/Ethyl Acetate/$H_2O$ | 2.50 |
| (d) Pyridine/MeOH/$H_2O$ | 1.00 |
| (e) DMSO/Acetone/$H_2O$ | 3.00 |

[1]DMF = dimethylformamide
[2]MeOH = methyl alcohol
[3]THF = tetrahydrofuran

Table II shows that the best procedure for making a highly sensitized product having the greatest air gap effectiveness entails the use of DMSO as the primary solvent, acetone as the secondary solvent and water as the tertiary solvent for precipitating the final product. Table II also shows some of the other solvent systems utilized in accordance with the principles of this invention which are effective to yield PYX explosives which are at least as sensitive as the PYX yielded by the process of the Pallanck patent.

Although the embodiments of the present invention which are now thought to be preferred have been described, it is understood that changes or modifications can be made in the invention without departing from the spirit and scope of the invention as defined in the following claims.

What is claimed is:

1. The method of preparing crystals of 2,6-bis(picrylamino)-3,5-dinitropyridine having improved high temperature explosive properties comprising:

dissolving one part by weight of 2,6-bis(picrylamino)-3,5-dinitropyridine in from about 2 to about 20 parts by weight of dimethylsulfoxide at a dissolution temperature of from about 70° C. to about 100° C. to form a primary solution;

combining at a temperature of from about 20° C. to about 100° C., the primary solution with a second solvent in which 2,6-(bis(picrylamino)-3,5-dinitropyridine is substantially insoluble, but which combines with the primary solution to form a transparent binary solvent system in which 2,6-bis(picrylamino)-3,5-dinitropyridine is soluble, said second solvent being selected from the group of solvents consisting of methanol, ethanol, 2-propanol, acetaldehyde, benzaldehyde, ethyl acetate, propyl acetate, butyl acetate, tetrahydrofuran, thiophene, 2-propanone, 2-butanone, cyclohexanone, methylethyl ketone acetonitrile and mixtures thereof which will combine with the primary solution to form a transparent binary solvent system, said secondary solvent being used in a volumetric ratio to said primary solvent of from about 10:1 to about 20:1;

adding to the binary solvent system, a third solvent which is miscible with the binary solvent system, and which upon such addition causes 2,6-bis(picrylamino)-3,5-dinitropyridine to be precipitated; then recovering the precipitated 2,6-bis(picrylamino)3,5-dinitropyridine from the solvent system from which it has been precipitated.

2. The method of preparing crystals of 2,6-bis(picrylamino)-3,5-dinitropyridine having improved high temperature explosive properties as defined in claim 1 wherein said third solvent is selected from the group of solvents consisting of water, ethylene glycol glycerine, acetic acid and formic acid.

3. The method of preparing crystals of 2,6-bis(picrylamino)-3,5-dinitropyridine having improved high temperature explosive properties as defined in claim 2 wherein the third solvent is water.

4. The method of preparing crystals of 2,6-bis(picrylamino)-3,5-dinitropyridine having improved high temperature explosive properties as defined in claim 1 wherein the second solvent is 2-propanone.

5. The method of preparing crystals of 2,6-bis(picrylamino)-3,5-dinitropyridine having improved high temperature explosive properties as defined in claim 1 wherein the amount of said third solvent added is at least equivalent in volume to the volume of primary solvent employed.

6. The method of preparing crystals of 2,6-bis(picrylamino)-3,5-dinitropyridine having improved high temperature explosive properties as defined in claim 5 wherein said second solvent is 2-propanone and said third solvent is water.

* * * * *